US009816982B2

(12) United States Patent
Bresolin et al.

(10) Patent No.: US 9,816,982 B2
(45) Date of Patent: Nov. 14, 2017

(54) DIAGNOSTIC APPARATUS

(71) Applicant: Advanced Animal Diagnostics, Inc., Durham, NC (US)

(72) Inventors: Stefano Bresolin, Garner, NC (US); David A. Calderwood, Chapel Hill, NC (US); Tobias M. Heineck, Durham, NC (US); David Newcomb, Morrisville, NC (US); Chris Paul, Hillsborough, NC (US); Jasper N. Pollard, Durham, NC (US); Rodolfo R. Rodriguez, Cary, NC (US); Demetris Young, Durham, NC (US)

(73) Assignee: Advanced Animal Diagnostics, Inc., Durham, NC (US)

( * ) Notice: Subject to any disclaimer, the term of this patent is extended or adjusted under 35 U.S.C. 154(b) by 1149 days.

(21) Appl. No.: 13/928,741

(22) Filed: Jun. 27, 2013

(65) Prior Publication Data
US 2014/0009596 A1 Jan. 9, 2014

Related U.S. Application Data

(60) Provisional application No. 61/667,691, filed on Jul. 3, 2012.

(51) Int. Cl.
*H04N 7/18* (2006.01)
*G01N 33/50* (2006.01)
(Continued)

(52) U.S. Cl.
CPC ......... *G01N 33/5094* (2013.01); *G02B 21/00* (2013.01); *G02B 21/0016* (2013.01);
(Continued)

(58) Field of Classification Search
CPC ....................................................... A61B 5/00
(Continued)

(56) References Cited

U.S. PATENT DOCUMENTS 3,574,064 A 4/1971 Binnings et al.
3,883,247 A 5/1975 Adams
(Continued)

FOREIGN PATENT DOCUMENTS

EP 1 965 209 A1 9/2008
WO WO 2004/094977 A2 11/2004
(Continued)

OTHER PUBLICATIONS

Molecular Devices. Multidimensional Acquisition: Auto Focus Dialog. Molecular Devices Article @T20125. Aug. 27, 2009. [Retrieved from internet on Nov. 22, 2013].
(Continued)

*Primary Examiner* — Andy Rao

(57) ABSTRACT

An automated microscope apparatus, comprises an outer housing having an external wall; optionally but preferably an internal wall in said housing, and configured to form a first compartment and a separate second compartment in said outer housing; a microscope assembly in said housing, preferably in said first compartment; and a microprocessor in said housing, preferably in said second compartment; and optionally but preferably a heat sink mounted on said housing external wall, preferably adjacent said second compartment, with said microprocessor thermally coupled to said heat sink and operatively associated with said microscope assembly.

13 Claims, 19 Drawing Sheets

(51) Int. Cl.
　　*G06T 7/00*　　　(2017.01)
　　*G02B 21/00*　　(2006.01)
　　*G06F 1/20*　　　(2006.01)
　　*G02B 21/26*　　(2006.01)

(52) U.S. Cl.
　　CPC ............... *G02B 21/26* (2013.01); *G06F 1/20* (2013.01); *G06T 7/0012* (2013.01); *G01N 2800/365* (2013.01)

(58) Field of Classification Search
　　USPC ..................................................... 348/79–80
　　See application file for complete search history.

(56) References Cited

U.S. PATENT DOCUMENTS

| | | | |
|---|---|---|---|
| 4,440,301 A | 4/1984 | Intengan | |
| 4,698,262 A | 10/1987 | Schwartz et al. | |
| 4,946,266 A | 8/1990 | Kraft et al. | |
| 5,367,401 A | 11/1994 | Saulietis | |
| 5,494,829 A | 2/1996 | Sandstrom et al. | |
| 6,627,621 B2 | 9/2003 | Nagaoka et al. | |
| 7,027,628 B1 | 4/2006 | Gagnon et al. | |
| 7,141,773 B2 | 11/2006 | Kaplan et al. | |
| 7,390,997 B2 | 6/2008 | Tohma | |
| 7,589,962 B1 | 9/2009 | Bhatia | |
| 7,861,768 B1 | 1/2011 | Ghantiwala | |
| 8,014,583 B2 | 9/2011 | Zahniser | |
| 9,052,315 B2 | 6/2015 | Rodriguez et al. | |
| 2001/0041347 A1 | 11/2001 | Sammak et al. | |
| 2002/0098588 A1 | 7/2002 | Sammak et al. | |
| 2002/0169394 A1* | 11/2002 | Eppstein ................. | A61B 5/00 600/573 |
| 2002/0187485 A1 | 12/2002 | Jakobsen et al. | |
| 2003/0127609 A1 | 7/2003 | El-Hage et al. | |
| 2004/0101912 A1 | 5/2004 | Rubin et al. | |
| 2005/0068614 A1 | 3/2005 | Yoneyama et al. | |
| 2007/0192882 A1 | 8/2007 | Dewald | |
| 2007/0242349 A1 | 10/2007 | Tafas | |
| 2008/0088918 A1 | 4/2008 | O'Connell | |
| 2008/0259566 A1 | 10/2008 | Fried | |
| 2008/0274538 A1 | 11/2008 | Mutz et al. | |
| 2009/0116101 A1 | 5/2009 | Tafas et al. | |
| 2009/0233329 A1 | 9/2009 | Rodriguez et al. | |
| 2010/0135861 A1 | 6/2010 | Sage et al. | |
| 2010/0328766 A1 | 12/2010 | Griffin et al. | |
| 2011/0117025 A1 | 5/2011 | Dacosta et al. | |
| 2012/0020537 A1 | 1/2012 | Garcia et al. | |
| 2012/0082361 A1 | 4/2012 | Burke et al. | |
| 2014/0009596 A1 | 1/2014 | Bresolin et al. | |

FOREIGN PATENT DOCUMENTS

| | | |
|---|---|---|
| WO | WO 2004/094977 A3 | 11/2004 |
| WO | WO 2008/002563 A2 | 1/2008 |
| WO | WO 2008/002563 A3 | 1/2008 |
| WO | WO 2011/113569 A1 | 9/2011 |

OTHER PUBLICATIONS

Elert G et al. Diameter of a Yeast. The Physics Factbook. 2000. [Retrieved from internet on Nov. 22, 2013].
International Search Report and Written Opinion, PCT/US2013/049112, dated Dec. 13, 2013.
International Search Report and Written Opinion, PCT/US2013/049247, dated Dec. 5, 2013.
European Office Action Corresponding to European Patent Application No. 13 724 126.1; dated: Feb. 24, 2016; 11 Pages.
European Search Report Corresponding to European Application No. 13 81 3619; dated Nov. 30, 2015; 8 Pages.
Xiao, Yan and Xiugong Gao. "Use of IgY antibodies and semiconductor nanocrystal detection in cancer biomarker quantitation", Biomarkers in Medicine, 4.2 (2010); 227-239.

\* cited by examiner

DIAGNOSTIC APPARATUS

RELATED APPLICATIONS

This application claims the benefit of U.S. Patent Application Ser. No. 61/667,691, filed Jul. 3, 2012, the disclosure of which is incorporated by reference herein in its entirety.

FIELD OF THE INVENTION

The present invention concerns diagnostic methods and apparatus, particularly methods and apparatus useful for detecting white blood cells or analytes in bodily fluids of production animals (for example, bovine mastitis in cattle from milk).

BACKGROUND OF THE INVENTION

Mastitis is the inflammation of the mammary gland caused by microorganisms that invade one or more quadrants of the bovine udder, multiply, and produce toxins that are harmful to the mammary gland. Economic loss to mastitis in the United States is estimated to be over 2 billion dollars. This is approximately 10% of the total value of farm milk sales, and about two-thirds of this loss is due to reduced milk production in subclinically infected cows.

In subclinical mastitis, there may be no visible signs of the disease, and diagnosis of subclinical mastitis may be performed by a somatic cell count (SCC) of the milk. The SCC is the number of leukocytes or white blood cells per volume of milk and is also used as an index of milk quality. It has also been recognized that there are multiple types of leukocytes, each with its own significance. In milk from a healthy animal, the predominant cell types are lymphocytes, followed by much lesser numbers of neutrophils and macrophages. The percentages of each kind of cell rise and fall as part of the immune response to infection. Those percentages, "the differential milk leukocyte count", represent the unique immune status of an individual quarter udder, at a specific point in time for better diagnosis of subclinical mastitis.

One method for detecting the differential milk leukocyte count is using flow-cytometry, which is an expensive, sophisticated tool typically only found in top research laboratories and generally not practical for the farmer. Another method for detecting the differential milk leukocyte count is the "manual milk differential smear" (MMDS), which is a difficult and time consuming procedure, and is subject to great variability, even when performed by highly trained laboratory technologists. Both flow-cytometry and MMDS present practical difficulties for field research or a barn environment.

U.S. Patent Application Publication No. 2009/0233329 to Rodriguez discloses a wedge microfluidic slide chamber for detecting mastitis or other diseases from a body fluid of a mammal, such as from cow's milk. While manual and automated procedures for carrying out disease detection with the aid of such a sample cartridge are described, again there is not described a system and apparatus useful for implementing such procedures in a field or barn environment.

SUMMARY OF THE INVENTION

A first aspect of the invention is an automated microscope apparatus, comprising: an outer housing having an external wall; optionally but preferably an internal wall in said housing, and configured to form a first compartment and a separate second compartment in said outer housing; a microscope assembly in said housing, preferably in said first compartment; and a microprocessor in said housing, preferably in said second compartment; and optionally but preferably a heat sink mounted on said housing external wall, preferably adjacent said second compartment, with said microprocessor thermally coupled to said heat sink and operatively associated with said microscope assembly.

In some embodiments, the microscope assembly comprises: a support frame; a subframe; a plurality of vibration isolators connecting said support frame to said subframe; an XYZ stage connected to said subframe; and an optical stage connected to said subframe. An XYZ drive assembly interconnecting said XYZ stage to said subframe is preferably included.

In some embodiments, the microprocessor is included as a passively cooled microprocessor assembly, comprising: a heat sink having a front surface and back surface; a circuit board having a front surface and back surface, with said microprocessor mounted on said circuit board front surface; a thermal coupler positioned between said microprocessor and said heat sink back surface, said thermal coupler fixed to and in thermal contact with said heat sink back surface; a clamp connected to said thermal coupler and configured to clamp said microprocessor to said thermal coupler, thereby placing said microprocessor, said thermal coupler, and said heat sink in thermal contact with one another.

In some embodiments, the XYZ stage is for securing a sample cartridge in the automated microscope having X, Y, and Z planes of movement, the sample cartridge having an end portion, a pair of generally parallel opposing side edge portions, and a locking edge portion formed thereon. The XYZ stage comprises a base member having a planar stage surface portion; a pair of generally parallel oppositely facing guide members on said planar stage surface and configured for slideably receiving said cartridge therebetween; and a locking member on said planar stage surface portion and positioned to press against the sample cartridge locking edge portion when said sample cartridge is inserted between said guide members, so that pressure is exerted by said lock member through said sample cartridge against at least one of said guide members, whereby the cartridge is removably locked in place on the XYZ stage in the Z plane.

A further aspect of the invention is an automated system for detecting a disorder in a subject, comprising: an XYZ stage configured to secure a sample cartridge; said sample cartridge comprising at least one chamber, said at least one chamber containing a biological sample collected from a subject; an imaging system operatively associated with said XYZ stage and configured to image selected cells in said sample, said selected cells including at least neutrophils; an autofocusing system operatively associated with said imaging system and said XYZ stage and configured to focus said imaging system on said at least one chamber; a processor running a software program or other suitable means for generating a count of at least neutrophils in said sample as an aid to detecting a disorder in said subject; and a controller configured to optionally repeat at least said imaging for at least one additional chamber on said cartridge.

The foregoing and other objects and aspects of the present invention are described in greater detail below. The disclosures of all U.S. Patent references cited herein are to be incorporated herein by reference.

DETAILED DESCRIPTION OF ILLUSTRATIVE EMBODIMENTS

Figure 1:
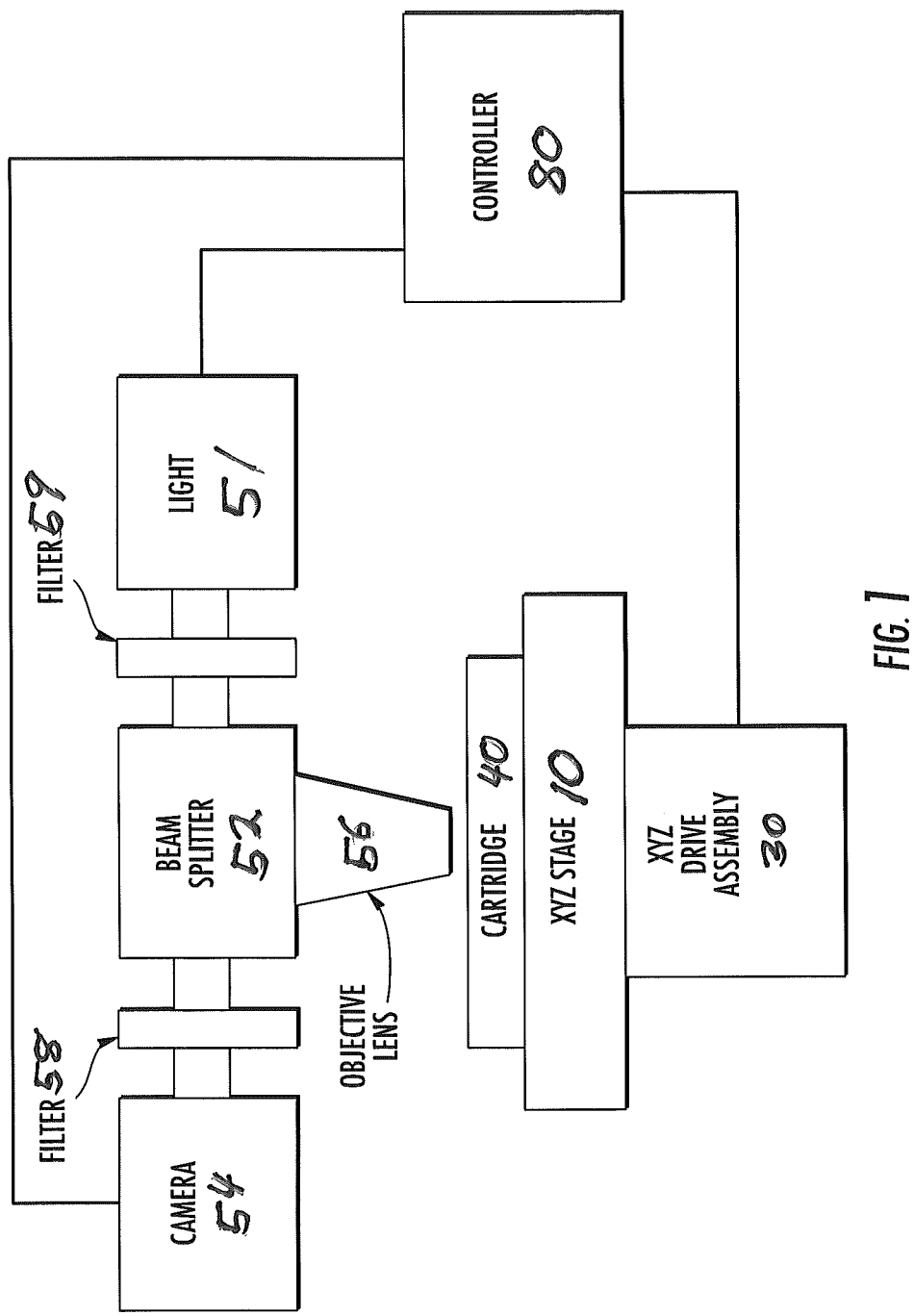
FIG. 1 is a partial schematic diagram of an apparatus of the present invention.

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

"Subject" as used herein includes both human and animal subjects for veterinary purposes, as well as plants for agricultural purposes. Examples of animal subjects include, but are not limited to, mammalian subjects such as dog, cat, cow, sheep, goat, llama, alpaca, camel, horse, pig, chicken, and turkey subjects.

Dairy animals such as cows, goats, sheep, buffalo, and camel, for the production of milk are particularly preferred for some embodiments of the invention.

"Milk" as used herein generally refers to mammalian milk of any species (e.g., cow, goat, human, etc.). The milk is typically raw milk, and is typically raw milk produced by dairy cattle after the production of colostrum has ceased, and generally intended for human consumption. The milk may optionally be diluted (typically with an aqueous diluent such as distilled water, saline solution, or buffer solution).

"Colostrum" as used herein is a form of milk produced by mammals in the first few days after birth, that may be higher in antibodies (for imparting passive immunity to offspring).

"Secretions" as used herein is a form of milk produced by mammals just prior to giving birth. Such secretions are sometimes also referred to as "colostrum" but in the present application "secretions" refers to the type of milk produced prior to the subject giving birth, while colostrum refers to the type of milk produced just after the subject giving birth.

"Sample cartridge" or "diagnostic cartridge" as used herein may be any suitable cartridge for containing a cell sample, including but are not limited to cartridges suitable for differential leukocyte analysis as described In R. Rodriguez and C. Galanaugh, U.S. Patent Application Publication No. 2009/0233329 (published Sep. 17, 2009), the disclosure of which is incorporated herein by reference in its entirety, and optionally incorporating the modifications or features discussed further below. In general, and as illustrated further below, such as cartridge includes at least one (e.g., two, four) sample chambers (e.g., a microfluidic chamber), which chamber or chambers may contain suitable cell or leukocyte observation colorants, stains, or reagents (e.g., reagents suitable for visualizing the cells under epifluorescent microscopy). The sample chambers are preferably aligned with one another on the cartridge (that is, on substantially the same Z plane as one another on the cartridge). In a preferred embodiment, each chamber contains reagents for separately and distinctly imaging or detecting neutrophils (or "polymorphonuclear leukocytes" (PMN)), lymphocytes, and macrophages, for differential leukocyte count diagnosis of infections such as bovine mastitis, in accordance with procedures known in the art, or which will be apparent to those skilled in the art based upon the instant disclosure, as discussed further below.

A partial schematic diagram of an apparatus of the present invention is given as an overview in FIG. 1. The apparatus comprises an XYZ stage (10) mounted on an XYZ drive assembly (30). A sample cartridge (40) is removably inserted into or engaged by the XYZ stage. The optical components for carrying out epifluorescent microscopy include a light or light source (51), a beam splitter (52), a camera (54), and an objective lens (56), all configured so that light from the source is directed onto the sample cartridge, and light emitted or fluoresced from the sample cartridge is directed to the camera. Filters (58, 59) are provided between the camera and beam splitter, and between the light source and beam splitter, so that the appropriate wavelengths of light are directed onto the sample cartridge, and the appropriate wavelengths of light are directed onto the camera. All components including the camera, light, and XYZ drive assembly, are controlled by any suitable controller (80), which may comprise a computer or processor with associated memory units, power, and control boards (not shown).

Individual components of the methods and apparatus described herein may be as known in the art, or variations thereof that will be apparent to those skilled in the art based on the instant disclosure and prior automated microscopy apparatus such as described in U.S. Pat. No. 4,998,284 to Bacus; U.S. Pat. No. 5,548,661 to Price; U.S. Pat. No. 5,790,710 to Price; U.S. Pat. No. 6,381,058 to Ramm; U.S. Pat. No. 6,929,953 to Wardlaw; U.S. Pat. No. 6,927,903 to Stuckey; U.S. Pat. No. 8,000,511 to Perz; U.S. Pat. No. 8,045,165 to Wardlaw; U.S. Pat. No. 8,081,303 to Levine; or U.S. Patent Application No. 2001/0041347 to Sammak.

Figure 2:
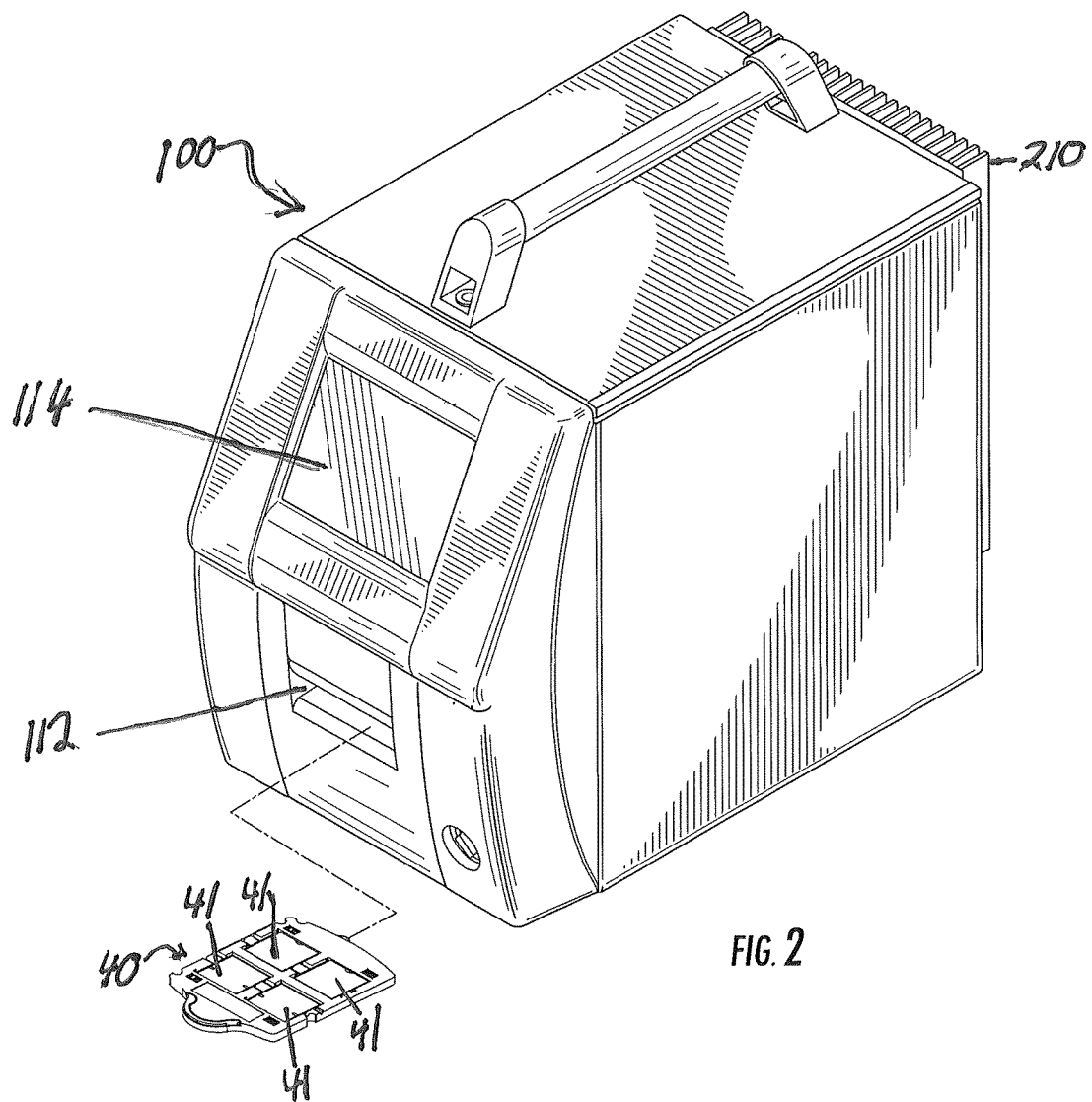
FIG. 2 is a perspective view of an apparatus of the present invention, with a sample cartridge to be inserted and touch screen user interface for input of information and display of results.

FIG. 2 is a perspective view of an apparatus (100) of the present invention, as constructed for portability and use in a dusty or otherwise harsh environment such as a barn or farm, or out-of-doors where animals to be diagnosed are found. All components of FIG. 1 above (and FIG. 3 below) are contained within the housing, except for the sample cartridge, which is removably inserted through a suitable opening (112) in the housing. A touch screen display (114) on the front of the device (e.g., an ESTECOM 6.5 inch intelligent panel LCD display/monitor) is provided to both display results and control the apparatus through its operational steps, as discussed further below.

Figure 3:
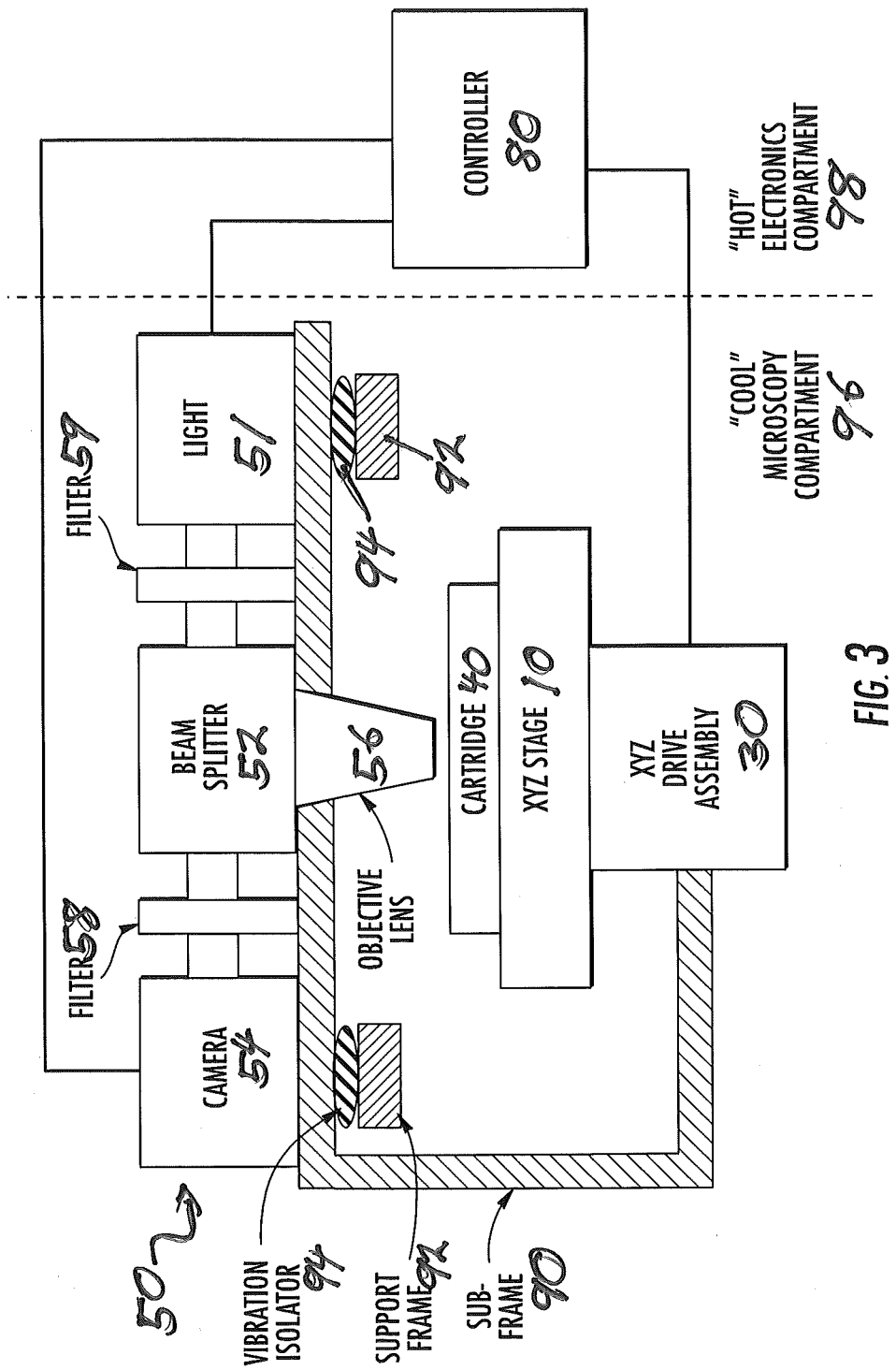
FIG. 3 is a schematic diagram of an apparatus of the present invention, showing vibration damping components and chamber separation.

FIG. 3 is a schematic diagram of an apparatus of the present invention similar to FIG. 1 above. In addition to the components shown in FIG. 1, additional features are now shown. The optical components (50) are shown as mounted on a subframe (90), which subframe is in turn mounted on a support frame (92) through vibration isolators (94). In addition, the microscopy components are shown as being contained within a separate, relatively cool, compartment (96) from the controller, which is in a relatively hot or warm compartment (98) (as compared to the microscopy compartment). The apparatus of FIG. 2 above incorporates these additional features, as discussed further below.

Figure 4:
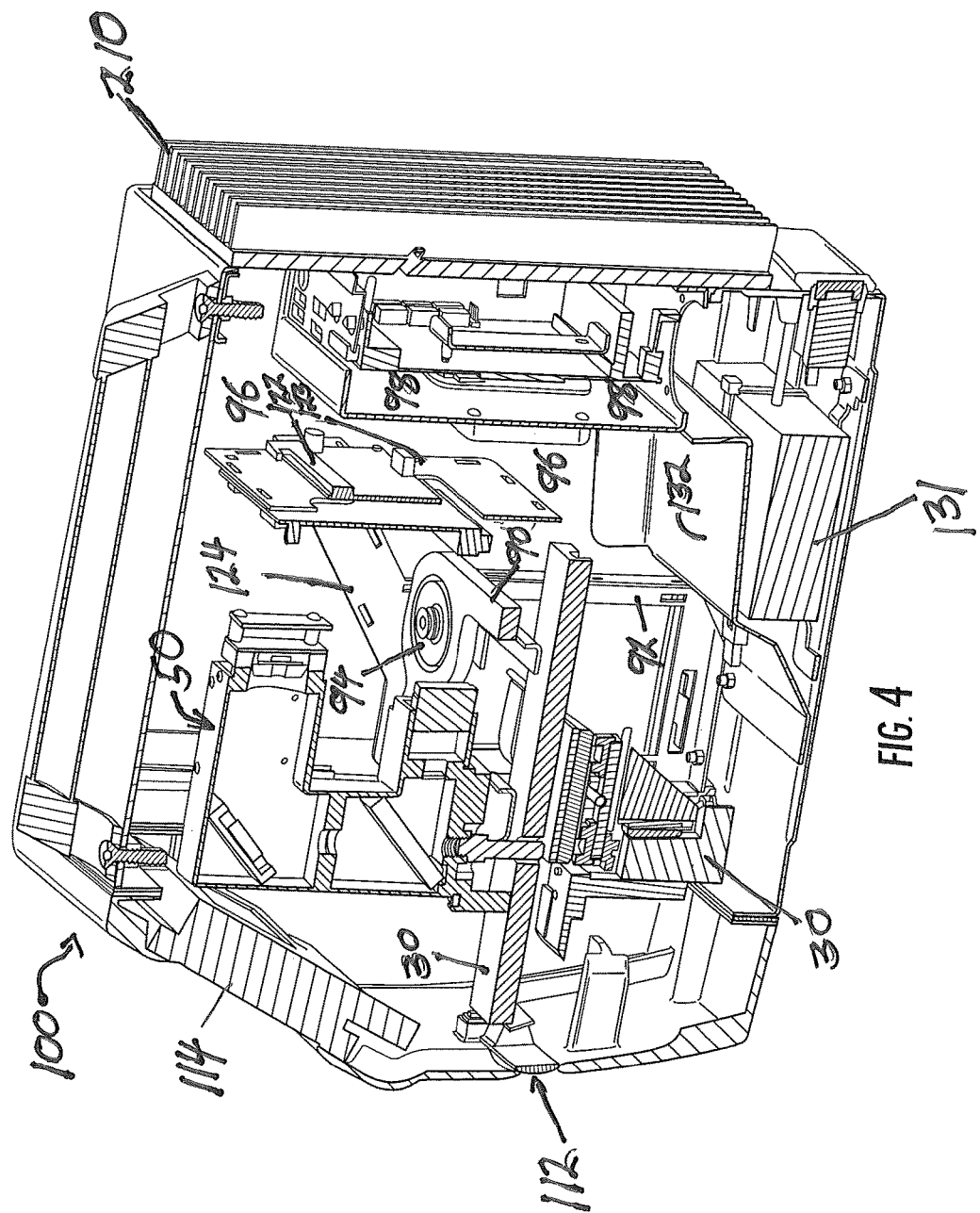
FIG. 4 is a cut-away perspective view of the apparatus of FIG. 2.

A partial cut-away perspective view of the apparatus of FIG. 2 is given in FIG. 4. A baseplate (90) serves a subframe for both the optical stage (50) and the XYZ drive assembly (30), which baseplate is in turn mounted through vibration dampening mounts (94) to the support frame (92). Any suitable active or passive vibration mount may be used, such as polymeric vibration mounts (e.g., those available from Stock Drive Products/Sterling Instruments, or any other suitable source).

An XYZ controller board (122) and a power distribution board (123) are conveniently located on a support bracket (124), which support bracket is mounted on the support frame (92), to facilitate assembly and testing of the microscopy compartment elements before they are placed into the housing, though numerous other configurations will be apparent to those skilled in the art.

A suitable power supply (131) (e.g., a fanless power supply such as MEAN WELL USP-350-12 350W power supply) is positioned in the bottom of the unit and covered by a shield or cable tray (132) (cables not shown for clarity) to prevent tangling of cables associated with the XYZ drive assembly, image sensor, and/or light, though numerous other configurations will be apparent, including location of the power supply external to the main housing.

A heat sink (210) is mounted on the back of the apparatus to cool the electronics compartment, as discussed further below.

Figure 5:
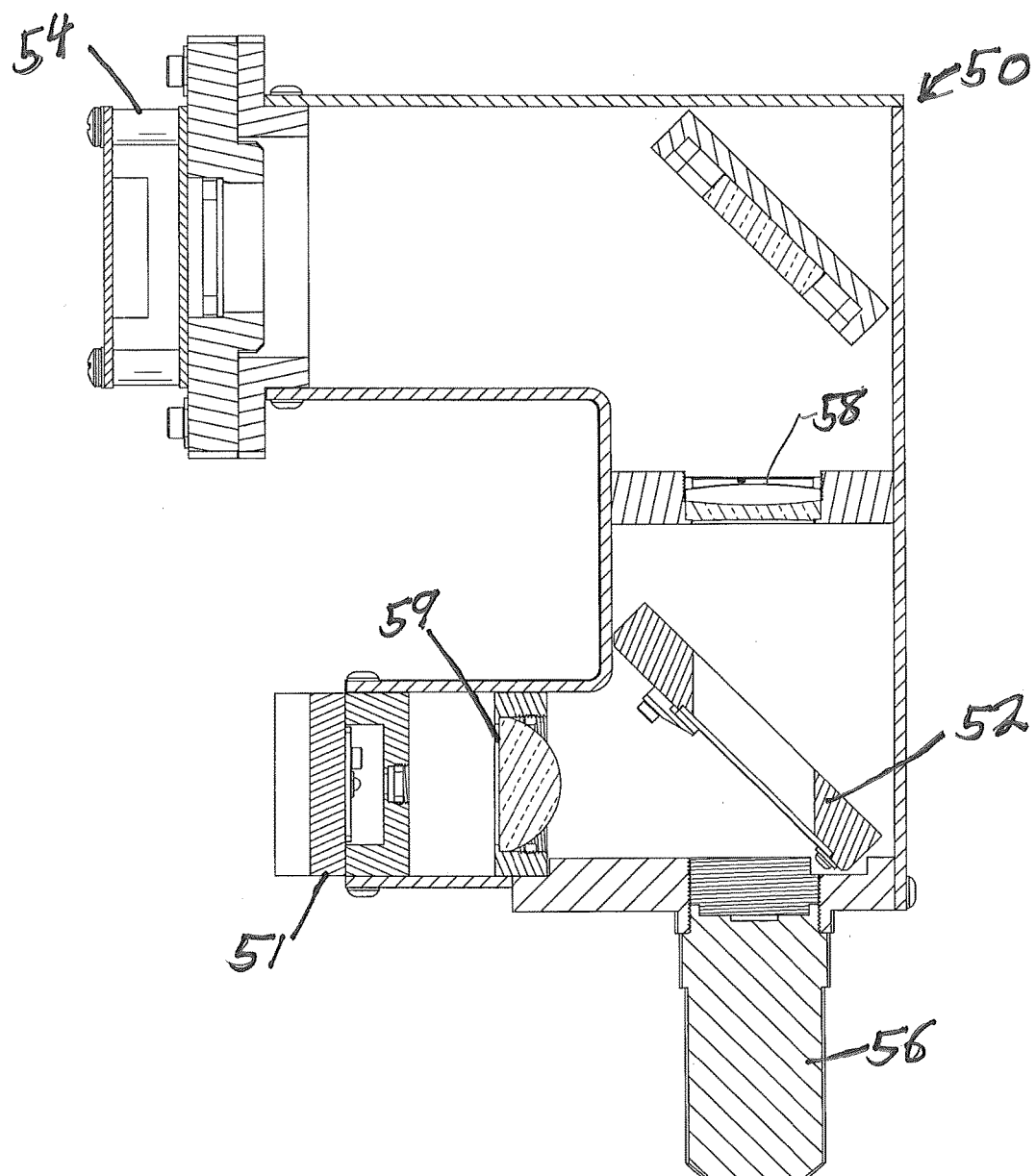
FIG. 5 is a side sectional view of an optical stage of the apparatus of FIG. 2, showing the light source, objective lens, filters, dichroic mirror and camera.

FIG. 5 is a side sectional view of an optical stage of the apparatus of FIG. 2, showing the light source, objective lens, filters including emission filters and excitation filters, dichroic mirror and image sensor (sometimes also referred to as "camera" herein), all contained within or connected to a common housing. Any suitable image sensor may be used, including CMOS image sensors, CCD image sensors, and hybrids thereof, typically 1 or 2 megapixel up to 10 or 20 megapixel, or more in resolution (e.g., a 5.0 megapixel OPTIC ANGLE image sensor). Any suitable light source may be used, including LED light (e.g. a CREE LED). Any suitable objective lens may be used, such as a 5× to 50× or 100× magnification objective lens (e.g., a NIKON MRL 00102 10× objective lens). In some embodiments, the light source is a 480 nm light source or LED; the emission filter is a dual pass filter with the center wavelength of 530 nm and 700 nm; the excitation filter has a center wave length of 470 nm, the dichroic mirror reflects 470 nm light and transmits light greater than 490 nm).

Figure 6:
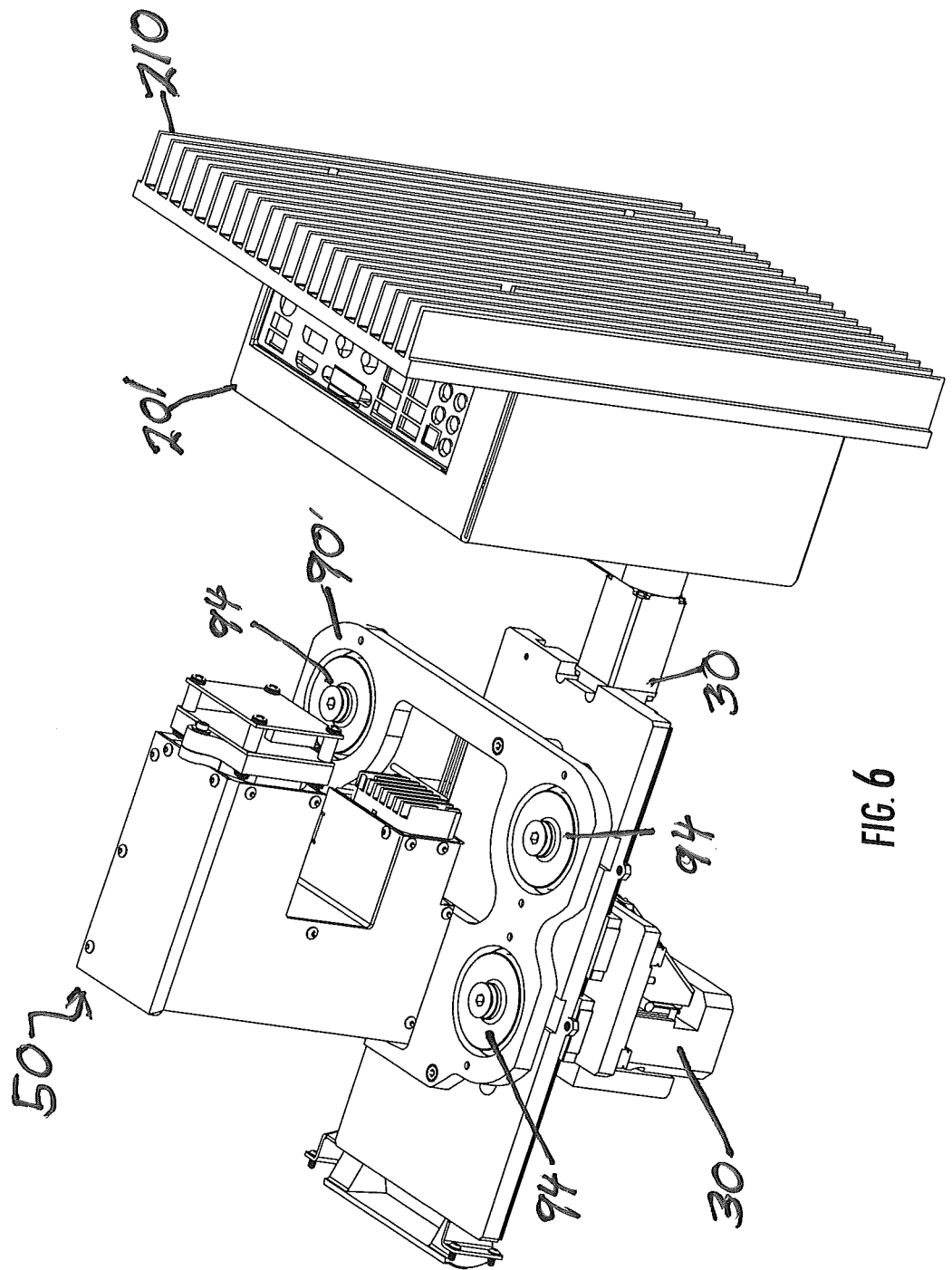
FIG. 6 is a perspective view of a microscope assembly and passively cooled microprocessor assembly of the apparatus of FIG. 2 with the cover removed and support frames removed.

The relationship of the major components of the microscopy compartment to the separate electronics compartment is shown in FIG. 6, which is a perspective view of a microscope assembly and passively cooled microprocessor assembly of the apparatus of FIG. 2 with the cover removed and support frame removed, showing the housing (201) surrounding the microprocessor board contained within the passively cooled electronics compartment. A solid state hard drive (not shown) may be conveniently mounted on the external surface of the electronics compartment housing to provide memory and storage, if desired, though again numerous other configurations will be readily apparent.

Figure 7:
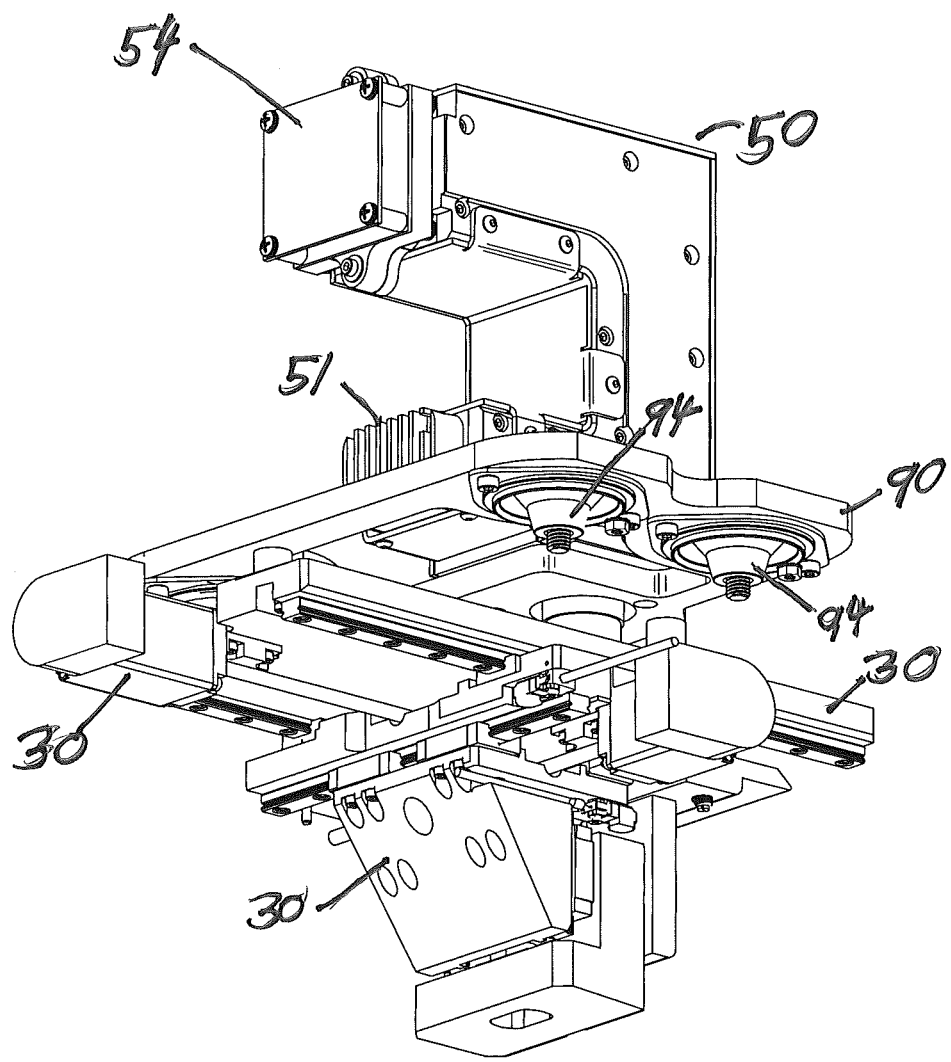
FIG. 7 is a perspective view of a microscope assembly of the apparatus of FIG. 2, with the support frame removed, showing the XYZ drive.
Figure 8:
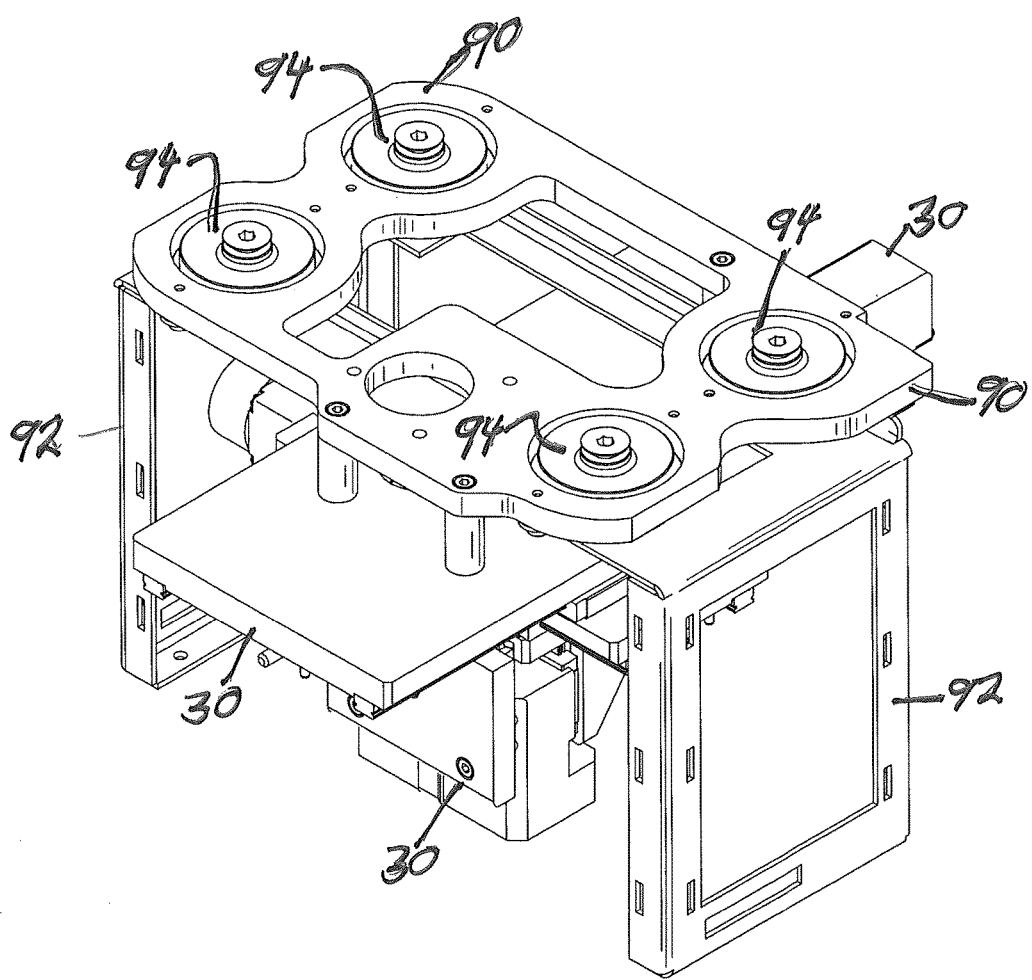
FIG. 8 is a perspective view of the mount, vibration dampers, and support frame of a microscope assembly of FIG. 2, upon which the optical stage of FIG. 5 is to be mounted.

The various components of the microscopy compartment are further illustrated in FIGS. 7-8. FIG. 7 is a lower perspective view of a microscope assembly of the apparatus of FIG. 2, showing the XYZ drive assembly mounted to the base plate (subframe), the optical stage mounted to the subframe, and the vibration isolation bushings, but with the support frame removed. Similarly, FIG. 8 is an upper perspective view of the base plate (subfame), XYZ drive assembly mounted on the base plate, mount, support frame upon which the base plate (subframe) is mounted through the vibration isolation bushings, but now with the optical stage removed.

Figure 9:
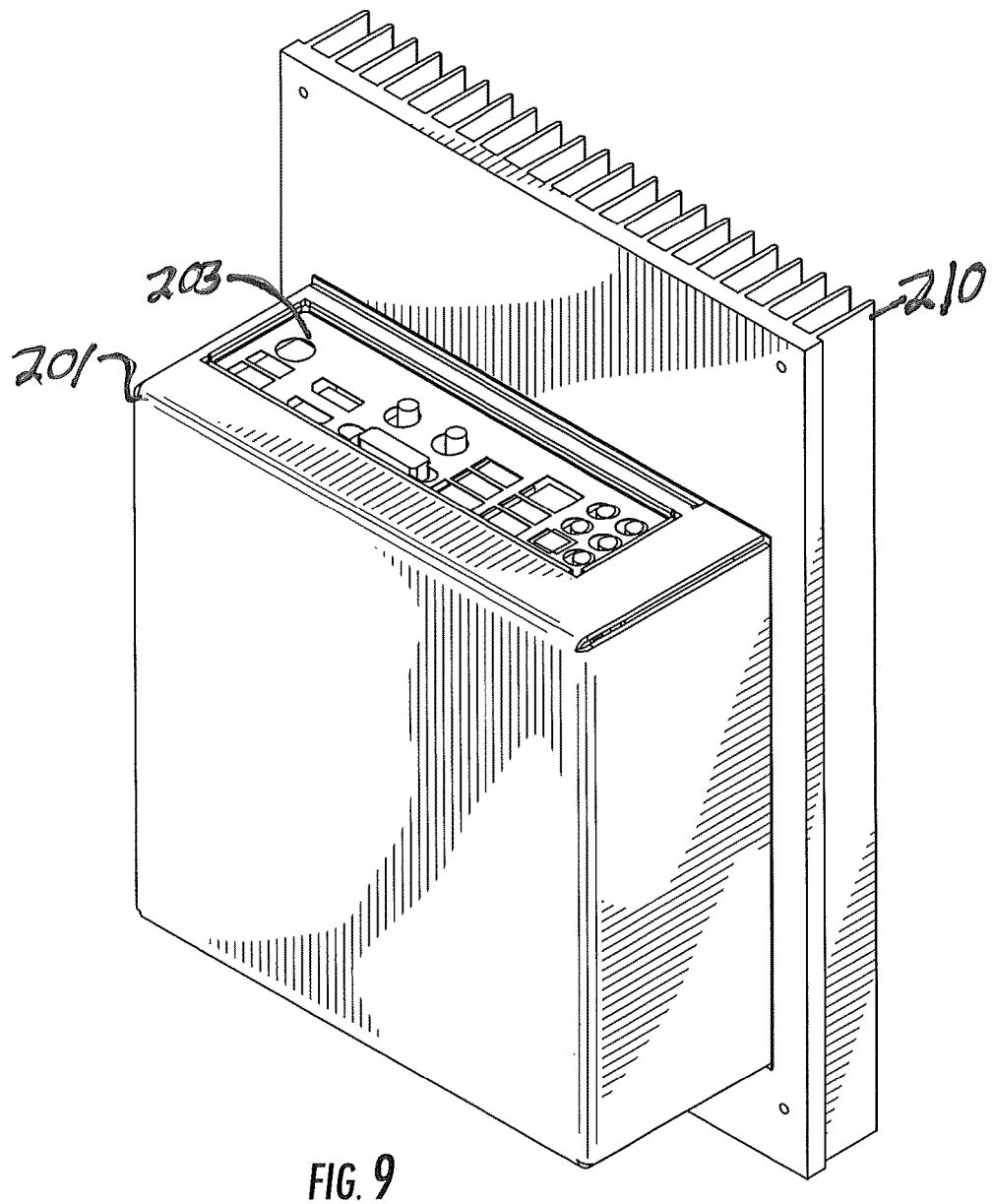
FIG. 9 is a perspective view of a passively cooled microprocessor assembly of the apparatus of FIG. 2.
Figure 10:
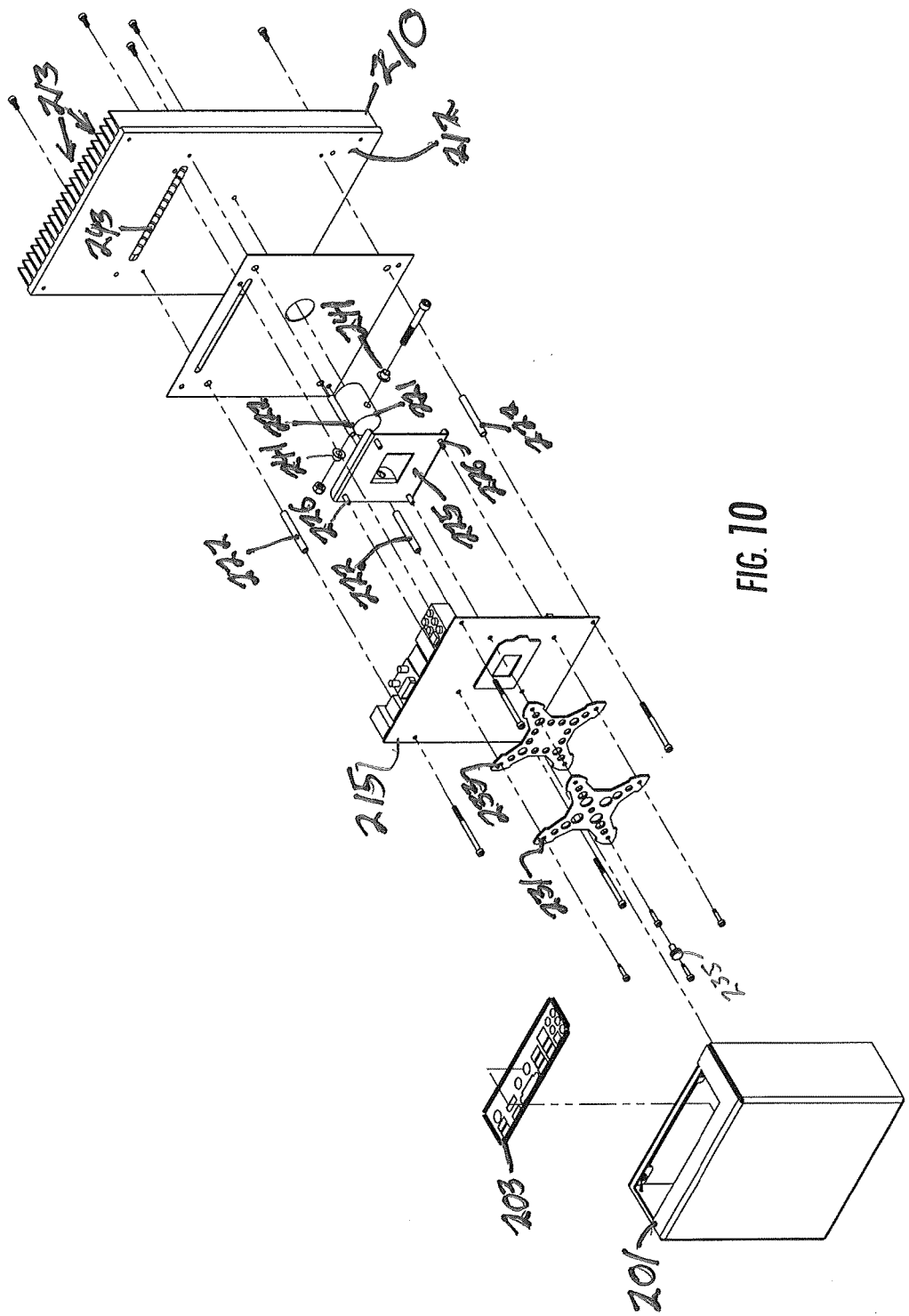
FIG. 10 is an exploded view of the microprocessor assembly of FIG. 9.
Figure 11:
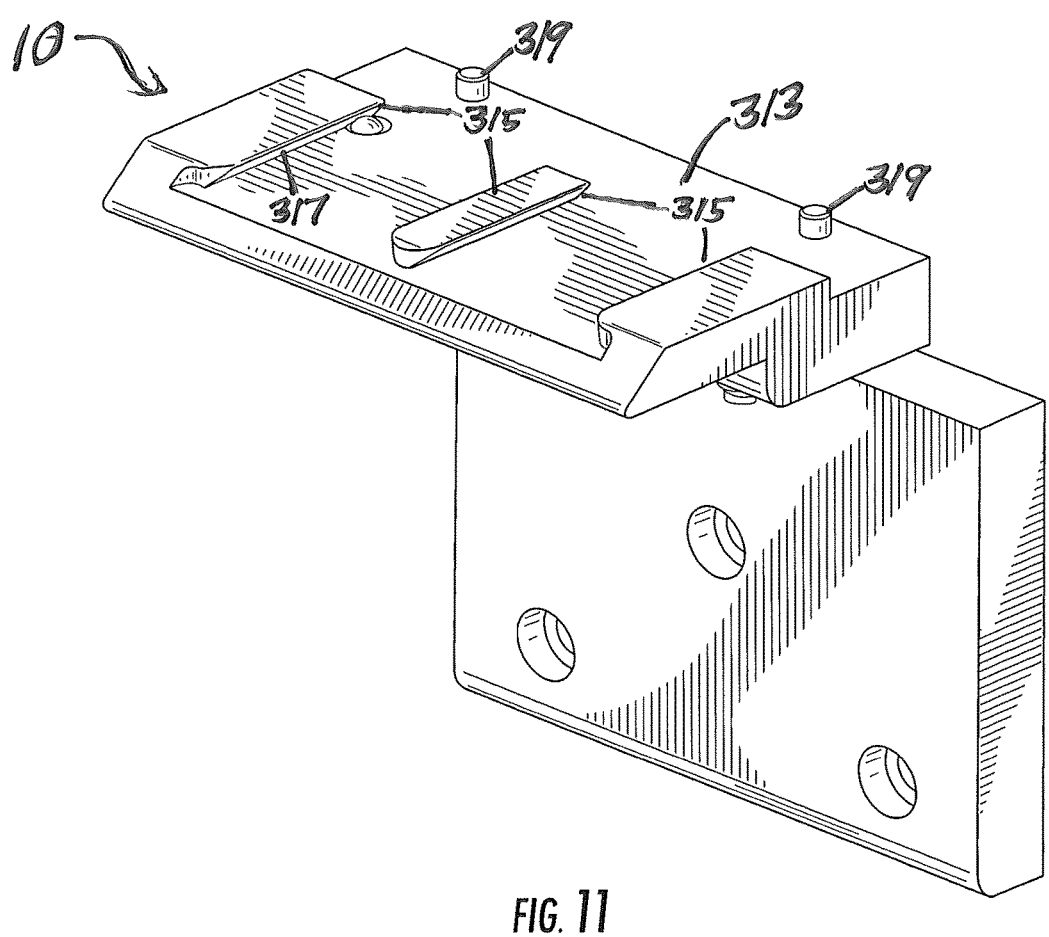
FIG. 11 is a perspective view of an XYZ stage of the apparatus of FIG. 2, as configured for retaining a pair of sample cartridges.
Figure 12:
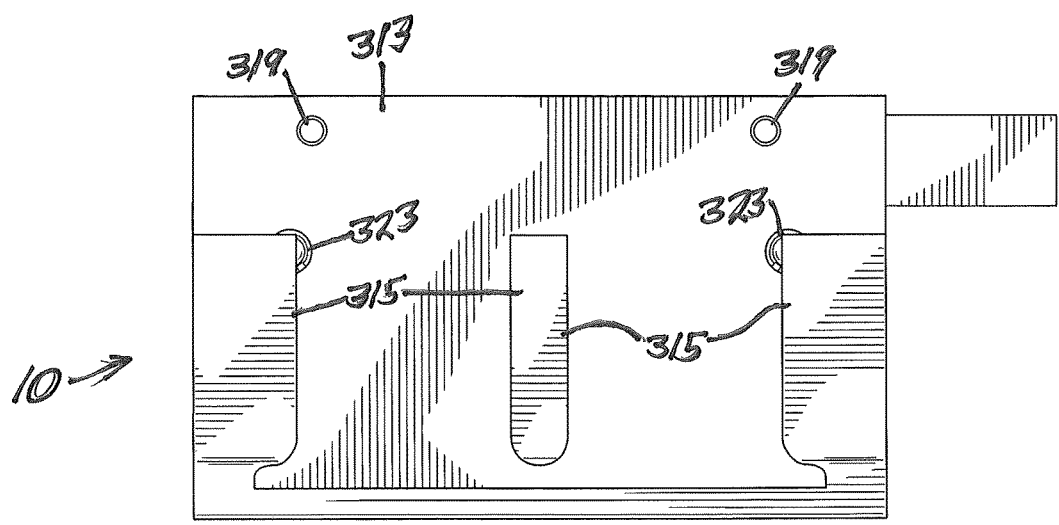
FIG. 12 is a top plan view of the XYZ stage of FIG. 11.
Figure 13:
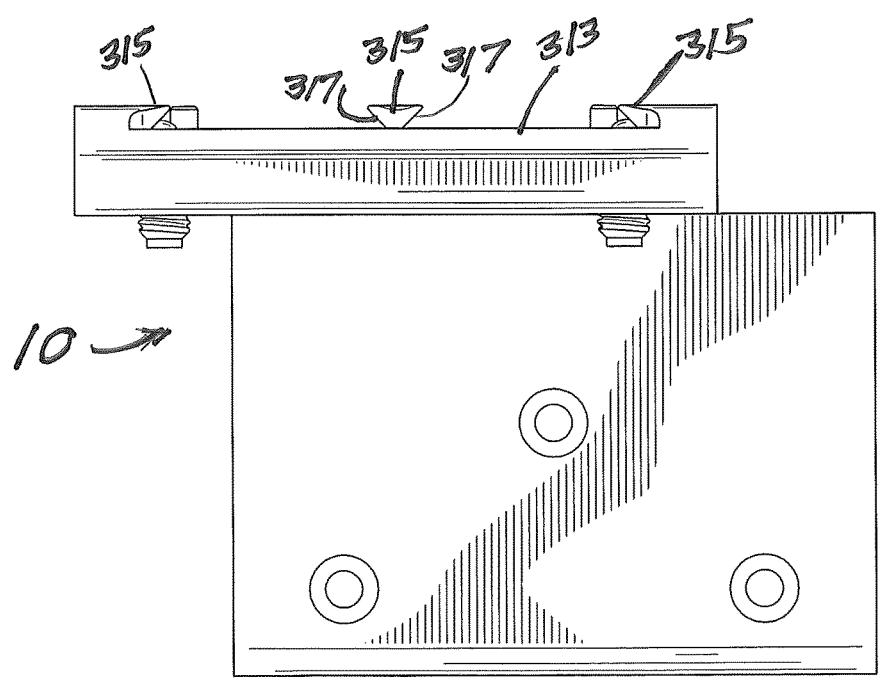
FIG. 13 is a side view of the XYZ stage of FIG. 11.
Figure 14:
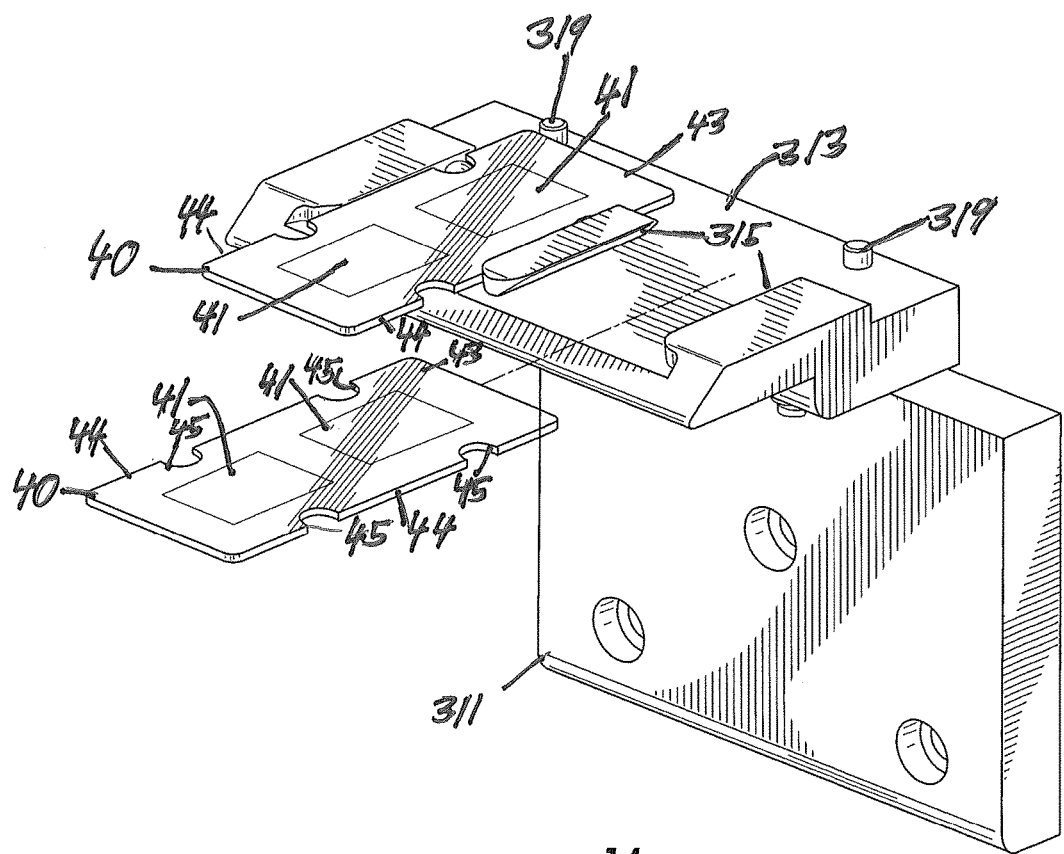
FIG. 14 is a perspective view of the XYZ stage of FIG. 11, showing a first sample cartridge seated in place, and a second sample cartridge to be inserted.

FIG. 9 is a perspective view of a passively cooled electronics compartment of the apparatus of FIG. 2, showing the electronics compartment housing (in which the microprocessor assembly is contained) mounted on the heat sink. An exploded view of this electronics compartment and microprocessor assembly is shown in FIG. 10. A mother board (e.g., a ZOTAC H67ITX-CE motherboard) is provided that carries a suitable microprocessor. Suitable microprocessors will generally be those having a thermal design power (or "TDP", sometimes also called "thermal design point") of at least 40, 50, or 60 Watts, up to 120, 140, or 160 Watts, or more. Suitable examples include, but are not limited to, Intel i7, Intel i5, and Intel i3 microprocessors.

As will be seen from FIGS. 9-10, a passively cooled microprocessor assembly includes a heat sink (210) having a front surface and back surface (212), the heat sink having cooling posts, fins or other suitable projections (213) formed on the front surface. A circuit board (215) or "mother board" having a front surface and back surface is included, with a microprocessor mounted on the circuit board front surface. A thermal coupler (221) (e.g., a copper slug or member; a heat pipe; etc.) is positioned between the microprocessor and said heat sink back surface, with the thermal coupler fixed to and in thermal contact with said heat sink back surface. A plurality of legs (222) are mounted on the heat sink back surface, with the circuit board mounted on the legs, and with the circuit board front surface spaced from and facing said heat sink back surface.

An anchor plate (225) is positioned around the microprocessor between the heat sink back surface and the circuit board front surface, with the anchor plate connected to the thermal coupler. A plurality of posts (226) are connected to the anchor plate and project through the circuit board, with a primary plate (231) connected to the posts opposite the anchor plate with the circuit board therebetween. A secondary plate (233) is slideably received on the plurality of posts and contacts said circuit board back surface. A screw (235) is threaded through the primary plate and contacts the secondary plate, so that tightening of the screw pushes the secondary plate against the circuit board back surface and clamps said microprocessor to said heat sink (optionally but preferably with a thermal grease sandwiched in between), thereby fixing the microprocessor, the thermal coupler, and the heat sink in thermal contact with one another. A housing (201) (e.g., a metal or aluminum) with an associated bezel (203) is provided around the assembly to form an electronics compartment (98) in the device separate from the microscopy compartment, as noted above. There is preferably included at least one thermal isolator (241) formed from a relatively thermally nonconductive material (e.g., an organic polymer), with the thermal coupler and the anchor plate are connected to one another through the at least one thermal isolator.

A ventilation opening (243) such as an elongated slot may optionally be formed in the heat sink to further facilitate cooling of the electronics chamber. Such an opening or port is preferably configured to inhibit or slow the progression of liquid or solid particles from outside the apparatus entering into the electronics chamber, such as by configuring the slot at a downward angle.

FIGS. 11 to 14 illustrate a first embodiment of an XYZ stage (10) of the apparatus of FIG. 2, as configured for retaining a pair of sample cartridges (40). As illustrated, each sample cartridge contains a pair of separate chambers (41), and the sample cartridges are reversibly insertable into the XYZ stage.

As shown in FIGS. 11 to 14, such a stage is configured to receive a sample cartridge having an end portion (43), a pair of generally parallel opposing side edge portions (44), and a locking edge portion formed (45) thereon, with each of said side edge portions having an upper corner portion, and with said locking edge portion positioned at an angle in relation to both said side portions and said front portion. The XYZ stage itself comprises a base member (311) having a planar stage surface portion (313), and a pair of generally parallel oppositely facing guide members (315) on said planar stage surface, each of said guide members having an inwardly angled edge portion (317) configured for contacting one of the cartridge side edge upper corner portions when the sample cartridge is inserted therebetween. A terminal block member (319) is provided on the planar stage surface portion and positioned to contact the sample cartridge end portion when the sample cartridge is inserted between said guide members. A locking member (323) (e.g., a spring-loaded ball detent) is included on the planar stage surface portion and positioned to press against the sample cartridge locking edge portion when the sample cartridge is inserted between the guide members and in contact with said terminal block, so that pressure is exerted by said lock member through said sample cartridge against both said terminal block and one of said guide members, whereby the cartridge is removably locked in place on the XYZ stage in at least the Z plane of movement, preferably all three of the X, Y and Z planes of movement, and still more preferably with the cartridge secured with reference to, or with respect to, the X, Y, and Z axes of rotation as well.

Figure 15:
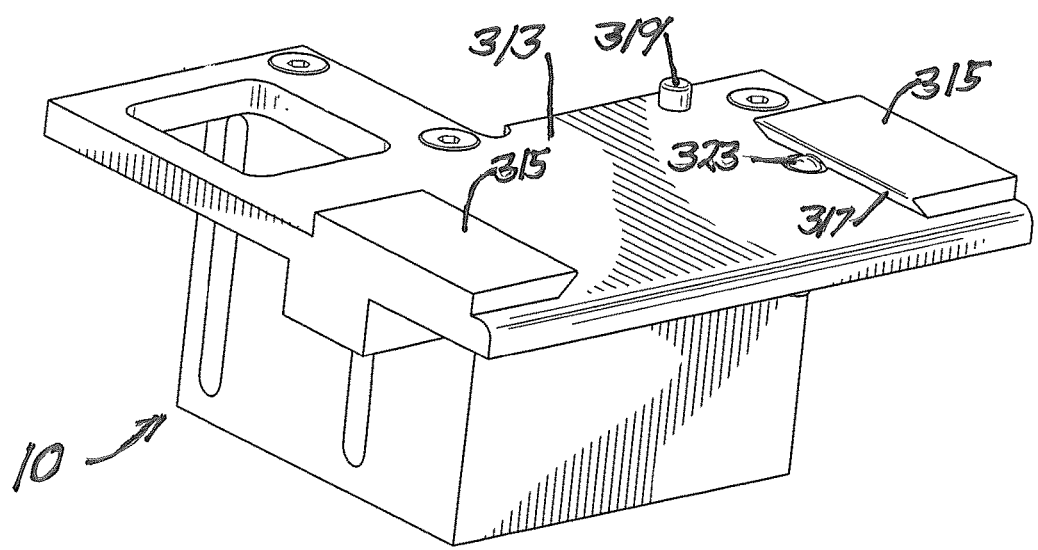
FIG. 15 is a perspective view of an alternate XYZ stage for an apparatus of FIG. 2, in which a single sample cartridge is to be inserted.
Figure 16:
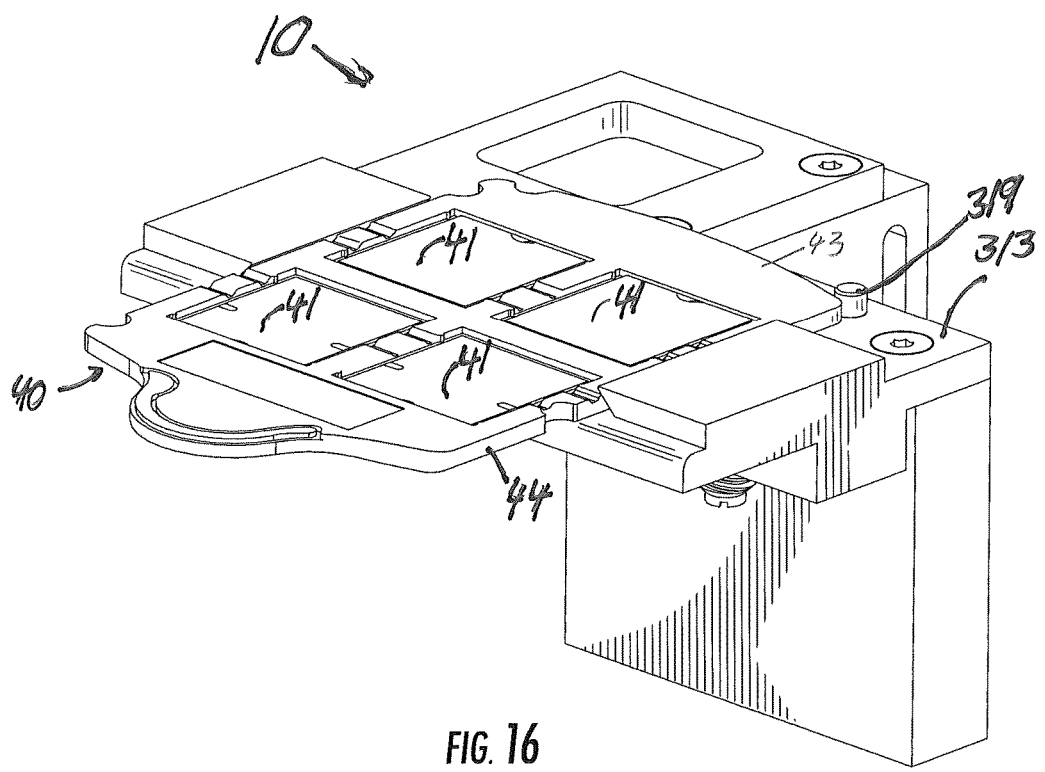
FIG. 16 is a perspective view of the XYZ stage of FIG. 15, with a sample cartridge inserted.

FIGS. 15 to 16 illustrate a second embodiment of an XYZ stage (10) of an apparatus of FIG. 2, as configured for retaining a single sample cartridge (40). Like components as compared found in FIGS. 11 to 14 are assigned like numbers. As illustrated in FIGS. 15-16, the sample cartridge contains four separate chambers (41) (sometimes also referred to as "quadrants" or "quads"), each of which may (for example) be used to contain a milk, colostrum or secretions sample from a separate one of each of the four teats of a cow's udder. As illustrated, the sample cartridge is nonreversible, or is configured so that it may be inserted into the XYZ stage in a single orientation only. When each teat of origin of a milk sample deposited within each chamber is identified or recorded, this facilitates identification of an infected teat or gland for subsequent treatment, and/or aids in identifying the severity or extent of infection of a particular cow.

Figure 17:
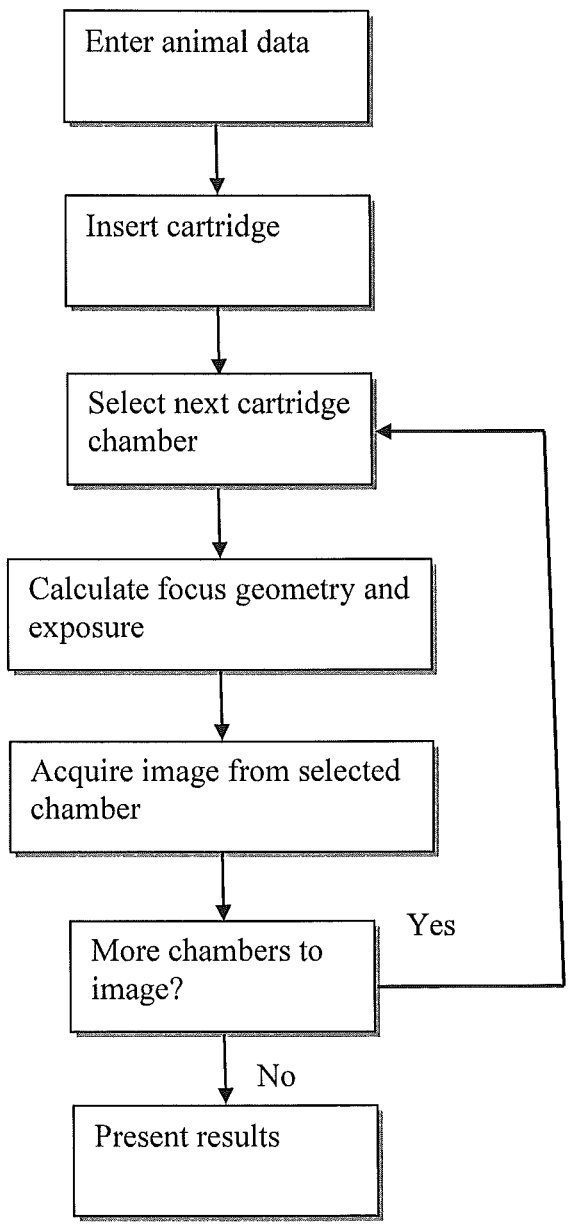
FIG. 17 is a schematic flow chart of a first mode of operation of an apparatus of FIG. 2 for detecting mastitis in cattle.

FIGS. 17 illustrate a mode of operating a device as described above, with FIGS. 18-23 illustrating the images displayed on (i.e., "screen shots" from) the user interface or "touch screen" of the apparatus of FIG. 2 described above. All components including the XYZ drive assembly, the light, the camera or imaging device, and the touch screen, may be operatively associated with and controlled by the controller or microprocessor as discussed above, programmed in a suitable language such as MICROSOFT C#.

Figure 18:
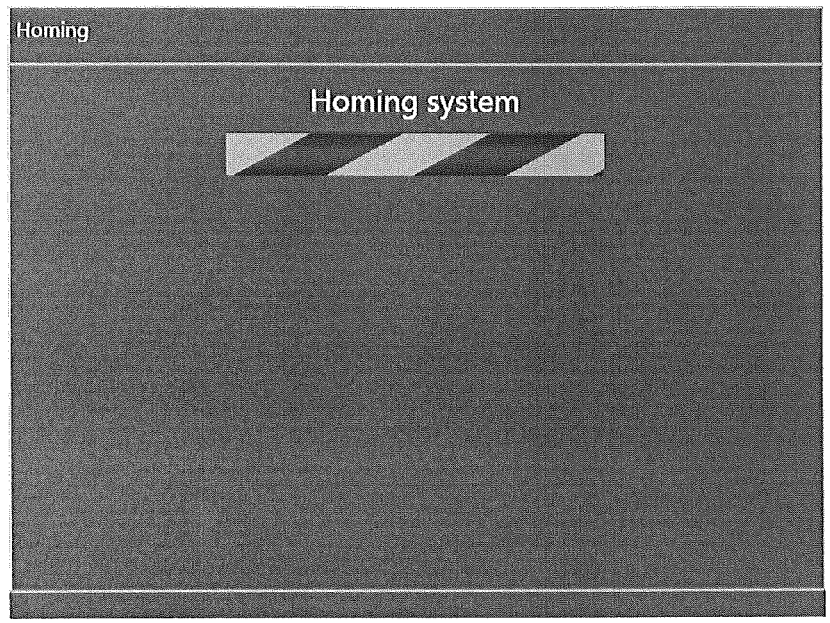
FIG. 18 illustrates the display of a user interface of an apparatus of FIG. 2 during homing of the optical stage.

Upon activating the system, the XYZ stage can be "horned" in accordance with known techniques, such as with electromechanical sensors, during which time a "homing" message such as shown in FIG. 18 may be displayed on the display screen.

Figure 19:
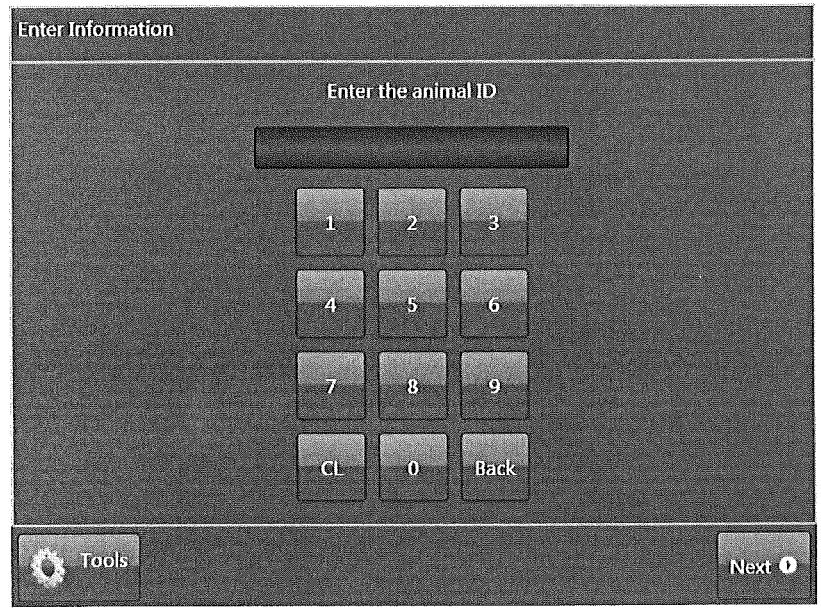
FIG. 19 illustrates the display of a user interface of an apparatus of FIG. 2 for input of animal data or information, particularly the identity of the animal from which the sample(s) are collected.
Figure 20:
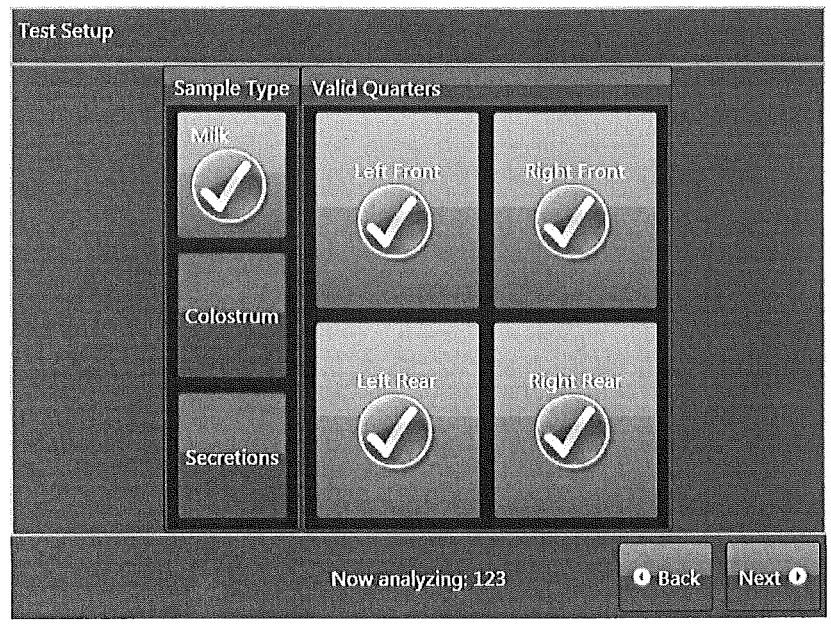
FIG. 20 illustrates the display of a user interface of an apparatus of FIG. 2 for input of animal data or information, particularly the type of sample collected, and the number of chambers in the sample cartridge for which sample imaging and analysis is to be carried out.

As shown in FIG. 17, following the process may begin (before or after "homing") by entering animal data, such as an animal identification or "ID" through a display interface such as shown in FIG. 19. Before or after animal identification is entered, the type of sample to be screened may be selected (e.g., milk, colostrum, secretions), and/or the number of separate chambers to be analyzed can be entered (which, in the case of a cow, can correspond to the quadrant of the mammary gland, and/or the specific teat, from which the sample is collected), such as through a suitable display and data entry screen such as shown in FIG. 20. Elimination of one or more chambers from the analysis procedure may advantageously reduce the overall time of the test.

Figure 21:
FIG. 21 illustrates the display of a user interface of an apparatus of FIG. 2 after homing and/or information entry is completed and when the apparatus is ready to receive the sample cartridge.

The sample cartridge may be inserted (before or after the entry of the animal data), optionally as prompted through the display of a "load sample" or "load cartridge" message such as given in FIG. 21. If desired, access to the cartridge carrier may be secured through a manually operated door, or an automated door controlled by the controller to open, and close, at the appropriate time in the operating cycle.

After the sample cartridge is inserted, the microscope is autofocused on the first sample chamber (as shown in FIG. 17) and imaging (including identification and counting of cells of interest) is carried out on the first sample chamber. Autofocusing may be carried out by any suitable technique, including but not limited to those described in U.S. Pat. Nos. 8,014,583; 7,141,773; 5,790,710; 5,647,025; 5,483,055; and 4,810,869, and variations thereof that will be apparent to those skilled in the art.

Figure 22:
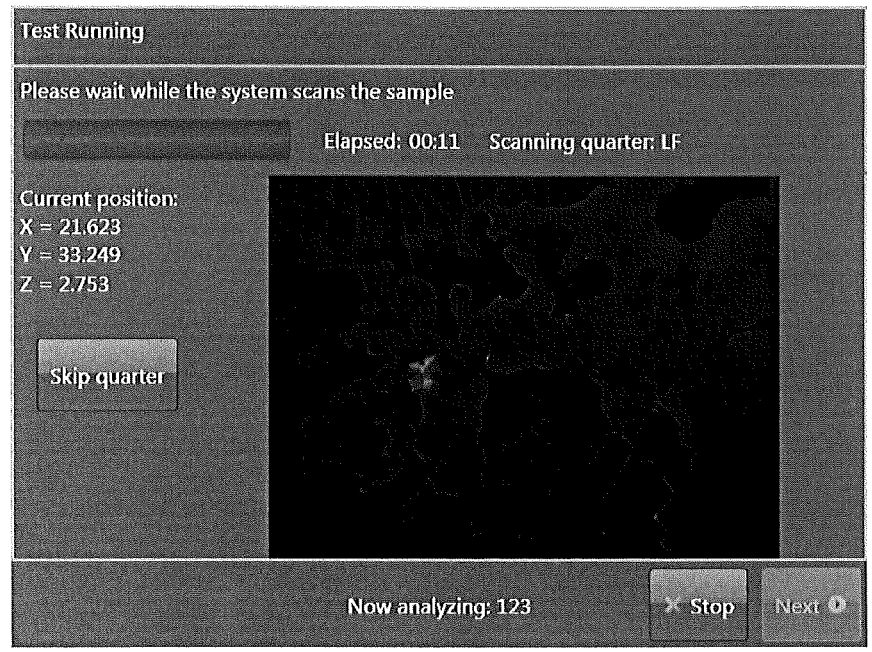
FIG. 22 illustrates the display of a user interface of an apparatus of FIG. 2 during image acquisition and analysis of one of the four separate chambers of a sample cartridge.

A display such as shown in FIG. 22 may optionally be provided during imaging, giving information such as the microscope image and the position (XY, and optionally Z) being scanned or imaged. Once imaging of the first chamber is completed, the optical stage is positioned by the controller over the next sample chamber to be imaged, again autofocused thereon as described above, and again imaged as described above. This process is repeated until all sample chambers have been imaged.

Identification and counting of cells can be carried out in accordance with known techniques or variations thereof that will be apparent to those skilled in the art. See, e.g., A. Katz, *Image Analysis and Supervised Learning in the Automated Differentiation of White Blood Cells from Microscopic Images*, Master's Thesis (Royal Melbourne Institute of Technology 2000); see also U.S. Pat. No. 7,991,213 to Tafas and U.S. Patent Application Nos. 2004/0085443 to Kallioniemi; 2011/0182490 to Hoyt; 2011/0255753 to Levenson; and 2011/0255745 to Hodder.

Determination of infection can be carried out from cell counts and identities in accordance with known techniques or variations thereof that will be apparent to those skilled in the art, such as by total leukocyte count or differential leukocyte count. See, e.g., Rodriguez and Galanaugh, supra; H. Tvedten et al., Automated differential leukocyte count in horses, cattle, and cats using the Technicon H-1E hematology system, *Vet, Clin Pathol.* 25, 14-22 (1996); G. Leitner et al., Milk leucocyte population patterns in bovine udder infection of different aetiology, *J. Vet. Med. B. Infect Dis. Vet. Public Health* 47, 581-89 (2000); H. Dosogne et al., Differential Leukocyte Count Method for Bovine Low Somatic Cell Count Milk, *J. Dairy Sci.* 86, 828-834 (2003); M. Albenzio et al., Differential Leukocyte Count for Ewe Milk with Low and High Somatic Cell Count, *J. Dairy Research* 78, 43-48 (2011).

Figure 23:
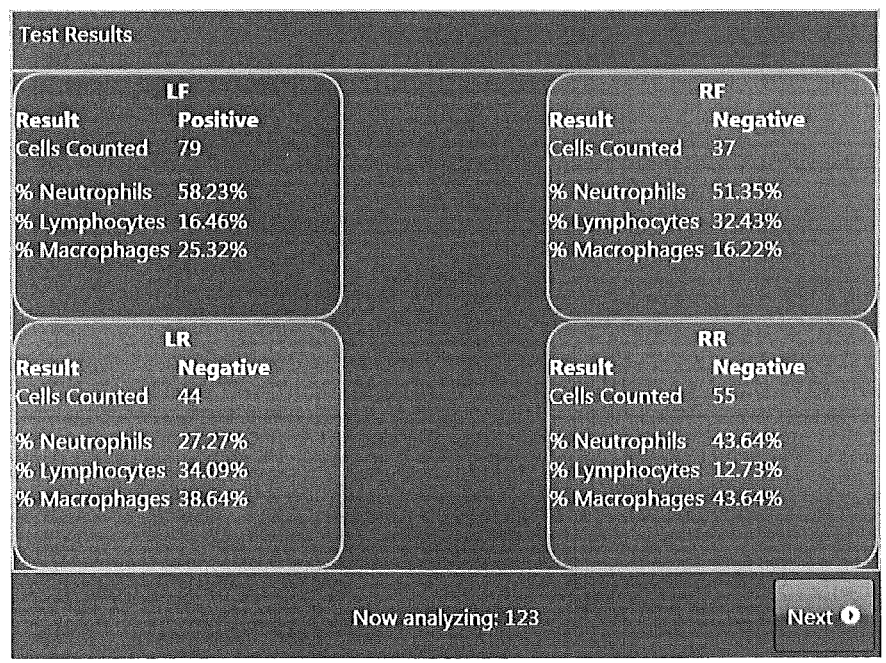
FIG. 23 illustrates the display of a user interface of an apparatus of FIG. 2 after image acquisition and differential leukocyte analysis has been completed. Note that one of the four quarters is indicated as "positive" for mastitis.

Results of imaging, identification, counting and analysis can be printed, stored on a suitable memory, and/or displayed on a final image screen such as that shown in FIG. 23.

The foregoing is illustrative of the present invention, and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

We claim:

1. An automated method to aid detecting a disorder in a subject, comprising:
    securing a sample cartridge to the stage of an automated microscope; said sample cartridge comprising at least one chamber, said at least one chamber containing a biological sample collected from a subject;
    autofocusing said microscope on said at least one chamber;
    imaging selected cells in said sample, said selected cells including at least neutrophils;
    generating a count of at least neutrophils in said sample as an aid to detecting a disorder in said subject; and
    optionally repeating at least said imaging step for at least one additional chamber on said cartridge,
    wherein:
    said subject is a dairy animal,
    said disorder is mastitis,
    said biological sample is selected from the group consisting of milk, secretions, or colostrum,
    said sample cartridge comprises from two to four chambers, and/or
    each chamber contains a milk sample collected from a different teat of said dairy animal.

2. The method of claim 1, wherein said disorder is an infection or inflammation.

3. The method of claim 1, wherein said sample cartridge comprises a plurality of chambers and said method further comprises the steps of:
    inputting selection of which of said chambers are to be imaged prior to said autofocusing step; and
    repeating said imaging step for said at least one additional chamber based on said input selection.

4. The method of claim 1, wherein said cartridge comprises two chambers.

5. The method of claim 1, wherein said cartridge comprises four chambers.

6. The method of claim 1, wherein said step of generating a count comprises generating a separate count for (a) neutrophils, (b) lymphocytes, and (c) macrophages.

7. The method of claim 1, further comprising the step of: determining the presence or absence of a disorder in said subject from said cell count.

8. The method of claim 7, wherein said determining step is carried out by differential leukocyte analysis.

9. The method of claim 1, wherein said cartridge comprises a plurality of chambers, and said autofocusing step is carried out separately for each of said chambers.

10. An automated system for detecting a disorder in a subject, comprising:
   an XYZ stage configured to secure a sample cartridge; said sample cartridge comprising at least one chamber, said at least one chamber containing a biological sample collected from a subject;
   an imaging system operatively associated with said XYZ stage and configured to image selected cells in said sample, said selected cells including at least neutrophils;
   an autofocusing system operatively associated with said imaging system and said XYZ stage and configured to focus said imaging system on said at least one chamber;
   means for generating a count of at least neutrophils in said sample as an aid to detecting a disorder in said subject;
   a controller configured to optionally repeat at least said imaging for at least one additional chamber on said cartridge, and
   means for determining the presence or absence of a disorder in said subject from said cell count, wherein said means for determining is carried out by differential leukocyte analysis, wherein:
   said subject is a dairy animal,
   said disorder is mastitis,
   said biological sample is selected from the group consisting of milk, secretions, or colostrum,
   said sample cartridge comprises from two to four chambers, and/or
   each chamber contains a milk sample collected from a different teat of said dairy animal.

11. The system of claim 10, wherein said disorder is an infection or inflammation.

12. The system of claim 10, wherein said sample cartridge comprises a plurality of chambers and said system further comprises:
   a user interface for inputting selection of which of said chambers are to be imaged prior to said autofocusing step; and
   a controller operatively associated with said user interface and configured for repeating said imaging step for said at least one additional chamber based on said input selection.

13. The system of claim 10, wherein said means for generating a count comprises means for generating a separate count for (a) neutrophils, (b) lymphocytes, and (c) macrophages.

* * * * *

UNITED STATES PATENT AND TRADEMARK OFFICE
CERTIFICATE OF CORRECTION

PATENT NO. : 9,816,982 B2
APPLICATION NO. : 13/928741
DATED : November 14, 2017
INVENTOR(S) : Bresolin et al.

Page 1 of 1

It is certified that error appears in the above-identified patent and that said Letters Patent is hereby corrected as shown below:

In the Specification

Column 9, Line 17: Please correct "horned" to read -- homed --

Signed and Sealed this
Tenth Day of July, 2018

Andrei Iancu
*Director of the United States Patent and Trademark Office*